(12) United States Patent
Reichen et al.

(10) Patent No.: US 8,425,603 B2
(45) Date of Patent: Apr. 23, 2013

(54) ORTHOPEDIC IMPLANT WITH FLEXIBLE KEEL

(75) Inventors: Marc Reichen, West Chester, PA (US); Kurt Schmura, Mohnton, PA (US)

(73) Assignee: Synthes USA, LLC, West Chester, PA (US)

( * ) Notice: Subject to any disclaimer, the term of this patent is extended or adjusted under 35 U.S.C. 154(b) by 483 days.

(21) Appl. No.: 12/641,441

(22) Filed: Dec. 18, 2009

(65) Prior Publication Data

US 2010/0168860 A1  Jul. 1, 2010

Related U.S. Application Data

(60) Provisional application No. 61/139,964, filed on Dec. 22, 2008.

(51) Int. Cl.
*A61F 2/44* (2006.01)
(52) U.S. Cl.
USPC ........................................ 623/17.11; 606/249
(58) Field of Classification Search .... 623/17.11–17.16; 606/246–249
See application file for complete search history.

(56) References Cited

U.S. PATENT DOCUMENTS

| | | | |
|---|---|---|---|
| 114,816 A | 5/1871 | Hiestand | |
| 3,486,505 A | 12/1969 | Morrison | |
| 3,579,829 A | 5/1971 | Sampson | |
| 3,875,595 A | 4/1975 | Froning | |
| 4,021,864 A | 5/1977 | Waugh | |
| 4,034,746 A | 7/1977 | Williams | |
| 4,038,897 A | 8/1977 | Murray et al. | |
| 4,038,987 A | 8/1977 | Komiya | |
| 4,232,404 A | 11/1980 | Samuelson et al. | |
| 4,309,777 A | 1/1982 | Patil | |
| 4,349,921 A | 9/1982 | Kuntz | |
| 4,467,802 A | 8/1984 | Maslanka | |
| 4,470,158 A | 9/1984 | Pappas et al. | |
| 4,545,374 A | 10/1985 | Jacobson | |
| 4,697,586 A | 10/1987 | Gazale | |
| 4,714,469 A | 12/1987 | Kenna | |
| 4,736,738 A | 4/1988 | Lipovsek et al. | |
| 4,759,766 A | 7/1988 | Buettner-Janz et al. | |
| 4,759,769 A | 7/1988 | Hedman et al. | |

(Continued)

FOREIGN PATENT DOCUMENTS

| DE | 2263842 | 7/1974 |
|---|---|---|
| DE | 2804936 | 8/1979 |

(Continued)

OTHER PUBLICATIONS

Hoogland, T., et al., 24$^{th}$ Annual ORS, Dallas, Texas, Feb. 21-23, 1978.

(Continued)

*Primary Examiner* — Eduardo C Robert
*Assistant Examiner* — Tara Carter
(74) *Attorney, Agent, or Firm* — Woodcock Washburn LLP

(57) ABSTRACT

A flexible keel is provided for use as a bone anchoring element for use with a range of orthopedic implants having portions configured for anchoring into boney tissue. The flexible keel includes two wings terminating proximally in a pair of outward flares, the wings further spaced from a bone contacting implant surface by a void. The flexibility of the keel wings increases the ease of revision or explantation procedures.

22 Claims, 9 Drawing Sheets

U.S. PATENT DOCUMENTS

| | | |
|---|---|---|
| 4,863,476 A | 9/1989 | Sheppard |
| 4,874,389 A | 10/1989 | Downey |
| 4,892,545 A | 1/1990 | Day et al. |
| 4,898,161 A | 2/1990 | Grundei |
| 4,932,975 A | 6/1990 | Main et al. |
| 4,946,378 A | 8/1990 | Hirayama et al. |
| 4,997,432 A | 3/1991 | Keller |
| 5,002,576 A | 3/1991 | Fuhrmann et al. |
| 5,037,438 A | 8/1991 | Davidson |
| 5,062,850 A | 11/1991 | MacMillan et al. |
| 5,071,437 A | 12/1991 | Steffee |
| 5,108,442 A | 4/1992 | Smith |
| 5,122,130 A | 6/1992 | Keller |
| 5,171,280 A | 12/1992 | Baumgartner |
| 5,192,327 A | 3/1993 | Brantigan |
| 5,211,645 A | 5/1993 | Baumgart et al. |
| 5,228,455 A | 7/1993 | Barcel |
| 5,236,460 A | 8/1993 | Barber |
| 5,258,031 A | 11/1993 | Salib et al. |
| 5,271,737 A | 12/1993 | Baldwin et al. |
| 5,290,312 A | 3/1994 | Kojimoto et al. |
| 5,306,308 A | 4/1994 | Gross et al. |
| 5,306,309 A | 4/1994 | Wagner et al. |
| 5,314,477 A | 5/1994 | Marnay |
| 5,336,232 A | 8/1994 | Green et al. |
| 5,344,458 A | 9/1994 | Bonutti |
| 5,364,397 A | 11/1994 | Hayes et al. |
| 5,370,697 A | 12/1994 | Baumgartner |
| 5,383,888 A | 1/1995 | Zvenyatsky et al. |
| 5,395,317 A | 3/1995 | Kambin |
| 5,401,269 A | 3/1995 | Buttner-Janz et al. |
| 5,409,492 A | 4/1995 | Jones et al. |
| 5,423,825 A | 6/1995 | Levine |
| 5,425,773 A | 6/1995 | Boyd et al. |
| 5,431,658 A | 7/1995 | Moskovich |
| 5,443,514 A | 8/1995 | Steffee |
| 5,484,437 A | 1/1996 | Michelson |
| 5,489,307 A | 2/1996 | Kuslich et al. |
| 5,501,654 A | 3/1996 | Failla et al. |
| 5,505,732 A | 4/1996 | Michelson |
| 5,507,816 A | 4/1996 | Bullivant |
| 5,509,934 A | 4/1996 | Cohen |
| 5,534,029 A | 7/1996 | Shima |
| 5,534,030 A | 7/1996 | Navarro et al. |
| 5,545,229 A | 8/1996 | Parsons et al. |
| 5,554,191 A | 9/1996 | Lahille et al. |
| 5,556,431 A | 9/1996 | Buttner-Janz et al. |
| 5,562,736 A | 10/1996 | Ray et al. |
| 5,562,738 A | 10/1996 | Boyd et al. |
| 5,571,109 A | 11/1996 | Bertagnoli |
| 5,591,235 A | 1/1997 | Kuslich |
| 5,609,636 A | 3/1997 | Kohrs et al. |
| 5,676,701 A | 10/1997 | Yuan et al. |
| 5,683,465 A | 11/1997 | Shinn et al. |
| 5,702,469 A | 12/1997 | Whipple et al. |
| 5,716,415 A | 2/1998 | Steffee |
| 5,720,751 A | 2/1998 | Jackson |
| 5,722,977 A | 3/1998 | Wilhelmy |
| 5,776,199 A | 7/1998 | Michelson |
| 5,782,830 A | 7/1998 | Farris |
| 5,782,832 A | 7/1998 | Larsen et al. |
| 5,797,909 A | 8/1998 | Michelson |
| 5,800,547 A | 9/1998 | Schafer et al. |
| 5,824,094 A | 10/1998 | Serhan et al. |
| D401,335 S | 11/1998 | Koros et al. |
| 5,865,848 A | 2/1999 | Baker |
| 5,885,300 A | 3/1999 | Tokuhashi et al. |
| 5,888,226 A | 3/1999 | Rogozinski |
| 5,895,428 A | 4/1999 | Berry |
| 5,897,593 A | 4/1999 | Kohrs et al. |
| 5,899,901 A | 5/1999 | Middleton |
| 5,899,941 A | 5/1999 | Nishijima et al. |
| 5,951,564 A | 9/1999 | Schroder et al. |
| 6,006,174 A | 12/1999 | Lin et al. |
| 6,010,502 A | 1/2000 | Bagby |
| 6,017,342 A | 1/2000 | Rinner |
| 6,019,792 A | 2/2000 | Cauthen |
| 6,033,405 A | 3/2000 | Winslow et al. |
| 6,036,692 A | 3/2000 | Burel et al. |
| 6,042,582 A | 3/2000 | Ray et al. |
| 6,059,790 A | 5/2000 | Sand et al. |
| 6,063,088 A | 5/2000 | Winslow |
| 6,063,121 A | 5/2000 | Xavier et al. |
| 6,080,155 A | 6/2000 | Michelson |
| 6,083,225 A | 7/2000 | Winslow et al. |
| 6,086,595 A | 7/2000 | Yonemura et al. |
| 6,096,038 A | 8/2000 | Michelson |
| 6,096,080 A | 8/2000 | Nicholson et al. |
| 6,102,950 A | 8/2000 | Vaccaro |
| 6,102,954 A | 8/2000 | Albrektsson et al. |
| 6,110,179 A | 8/2000 | Flivik et al. |
| 6,113,602 A | 9/2000 | Sand |
| 6,113,637 A | 9/2000 | Gill et al. |
| 6,113,638 A | 9/2000 | Williams et al. |
| 6,117,174 A | 9/2000 | Nolan |
| 6,126,660 A | 10/2000 | Dietz |
| 6,126,674 A | 10/2000 | Janzen |
| 6,146,421 A | 11/2000 | Gordon et al. |
| 6,156,040 A | 12/2000 | Yonemura et al. |
| 6,156,067 A | 12/2000 | Bryan et al. |
| 6,159,215 A | 12/2000 | Urbahns et al. |
| 6,171,339 B1 | 1/2001 | Houfburg et al. |
| 6,174,311 B1 | 1/2001 | Branch et al. |
| 6,224,599 B1 | 5/2001 | Baynham et al. |
| 6,238,414 B1 | 5/2001 | Griffiths |
| 6,241,769 B1 | 6/2001 | Nicholson et al. |
| 6,251,140 B1 | 6/2001 | Marino et al. |
| 6,261,296 B1 | 7/2001 | Aebi et al. |
| 6,264,655 B1 | 7/2001 | Pisharodi |
| 6,270,498 B1 | 8/2001 | Michelson |
| 6,309,421 B1 | 10/2001 | Pisharodi |
| 6,368,350 B1 | 4/2002 | Erickson et al. |
| 6,368,351 B1 | 4/2002 | Glenn et al. |
| 6,402,785 B1 | 6/2002 | Zdeblick et al. |
| 6,413,278 B1 | 7/2002 | Marchosky |
| 6,436,139 B1 | 8/2002 | Shapiro et al. |
| 6,440,142 B1 | 8/2002 | Ralph et al. |
| 6,440,168 B1 | 8/2002 | Cauthen |
| 6,440,169 B1 | 8/2002 | Elberg et al. |
| 6,447,547 B1 | 9/2002 | Michelson |
| 6,478,800 B1 | 11/2002 | Fraser et al. |
| 6,478,801 B1 | 11/2002 | Ralph et al. |
| 6,478,823 B1 | 11/2002 | Michelson |
| 6,500,206 B1 | 12/2002 | Bryan |
| 6,517,544 B1 | 2/2003 | Michelson |
| 6,558,424 B2 | 5/2003 | Thalgott |
| 6,565,574 B2 | 5/2003 | Michelson |
| 6,595,995 B2 | 7/2003 | Zdeblick et al. |
| 6,599,294 B2 | 7/2003 | Fuss et al. |
| 6,610,065 B1 | 8/2003 | Branch et al. |
| 6,613,091 B1 | 9/2003 | Zdeblick et al. |
| 6,635,060 B2 | 10/2003 | Hanson et al. |
| 6,638,310 B2 | 10/2003 | Lin et al. |
| 6,641,582 B1 | 11/2003 | Hanson et al. |
| 6,641,614 B1 | 11/2003 | Wagner et al. |
| 6,652,533 B2 | 11/2003 | O'Neil |
| 6,652,534 B2 | 11/2003 | Zucherman et al. |
| 6,712,825 B2 | 3/2004 | Aebi et al. |
| 6,719,794 B2 | 4/2004 | Gerber et al. |
| 6,733,505 B2 | 5/2004 | Li |
| 6,740,118 B2 | 5/2004 | Eisermann et al. |
| 6,743,256 B2 | 6/2004 | Mason |
| 6,743,257 B2 | 6/2004 | Castro |
| 6,746,454 B2 | 6/2004 | Winterbottom et al. |
| 6,755,841 B2 | 6/2004 | Fraser et al. |
| 6,770,074 B2 | 8/2004 | Michelson |
| 6,824,565 B2 | 11/2004 | Muhanna et al. |
| 6,875,213 B2 | 4/2005 | Michelson |
| 6,896,676 B2 | 5/2005 | Zubok et al. |
| 6,936,071 B1 | 8/2005 | Marnay et al. |
| 6,964,687 B1 | 11/2005 | Bernerd et al. |
| 6,966,912 B2 | 11/2005 | Michelson |
| 7,081,120 B2 | 7/2006 | Li et al. |
| 7,118,580 B1 | 10/2006 | Beyersdorff et al. |
| 7,169,182 B2 | 1/2007 | Errico et al. |
| 7,189,234 B2 | 3/2007 | Zucherman et al. |
| 7,204,852 B2 | 4/2007 | Marnay et al. |

| | | |
|---|---|---|
| 7,238,203 B2 | 7/2007 | Bagga et al. |
| 7,252,673 B2 | 8/2007 | Lim |
| 7,491,204 B2 | 2/2009 | Marnay |
| 7,547,309 B2 | 6/2009 | Bertagnoli et al. |
| 7,575,576 B2 | 8/2009 | Zubok et al. |
| 7,625,380 B2 | 12/2009 | Drewry et al. |
| 7,763,024 B2 | 7/2010 | Bertagnoli et al. |
| 7,905,921 B2 | 3/2011 | Kim et al. |
| 2003/0083747 A1 | 5/2003 | Winterbottom et al. |
| 2003/0135275 A1 | 7/2003 | Garcia et al. |
| 2003/0233097 A1 | 12/2003 | Ferree |
| 2004/0030387 A1 | 2/2004 | Landry et al. |
| 2004/0143332 A1 | 7/2004 | Krueger et al. |
| 2004/0215198 A1 | 10/2004 | Marnay et al. |
| 2004/0225295 A1 | 11/2004 | Zubok et al. |
| 2004/0260286 A1 | 12/2004 | Ferree |
| 2005/0021042 A1 | 1/2005 | Marnay et al. |
| 2005/0085917 A1 | 4/2005 | Marnay et al. |
| 2005/0143747 A1 | 6/2005 | Zubok et al. |
| 2005/0143749 A1 | 6/2005 | Zalenski et al. |
| 2005/0165408 A1 | 7/2005 | Puno et al. |
| 2005/0251260 A1 | 11/2005 | Gerber et al. |
| 2005/0267581 A1 | 12/2005 | Marnay et al. |
| 2006/0030860 A1 | 2/2006 | Peterman |
| 2006/0089656 A1 | 4/2006 | Allard et al. |
| 2006/0100633 A1 | 5/2006 | Michelson |
| 2006/0149273 A1 | 7/2006 | Ross et al. |
| 2006/0241641 A1 | 10/2006 | Albans et al. |
| 2007/0010826 A1 | 1/2007 | Rhoda |
| 2007/0016221 A1 | 1/2007 | Beyersdorff et al. |
| 2007/0055378 A1* | 3/2007 | Ankney et al. ............. 623/17.15 |
| 2007/0162134 A1 | 7/2007 | Marnay et al. |
| 2007/0265707 A1 | 11/2007 | Marnay et al. |
| 2010/0076443 A1 | 3/2010 | Bertagnoli et al. |
| 2012/0109316 A1 | 5/2012 | Marnay |

FOREIGN PATENT DOCUMENTS

| | | |
|---|---|---|
| DE | 3023353 | 4/1981 |
| DE | 3526742 | 1/1987 |
| DE | 29916078 U1 | 11/1999 |
| EP | 0077159 | 4/1983 |
| EP | 0333990 A2 | 9/1989 |
| EP | 0712607 | 5/1996 |
| FR | 2718635 A | 10/1995 |
| FR | 2724108 | 3/1996 |
| FR | 2737656 | 2/1997 |
| FR | 2742653 | 6/1997 |
| FR | 2795945 A1 | 1/2001 |
| JP | 2261446 | 10/1990 |
| WO | WO 91/13598 A1 | 9/1991 |
| WO | WO 98/14142 | 4/1998 |
| WO | WO 98/34552 A1 | 8/1998 |
| WO | WO 01/01893 | 1/2001 |
| WO | WO 01/19295 A1 | 3/2001 |
| WO | WO 02/071986 A2 | 9/2002 |
| WO | WO 03/053290 A1 | 7/2003 |
| WO | WO 2007/140382 | 12/2007 |
| WO | WO 2008/16872 A3 | 2/2008 |

OTHER PUBLICATIONS

International Patent Application No. PCT/US2009/068636: International Search Report dated May 17, 2010, 5 pages.

International Patent Application No. PCT/US2009/068636: Written Opinion of the International Searching Authority, dated May 17, 2010, 5 pages.

*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Answer and Counterclaim (including affirmative defenses), May 4, 2007.

*Spine Solutions, Inc.* v. *Medtronic Sofamor Danek, Inc. and Medtronic Sofamor Danek USA, Inc.*, U.S. District Court, Western District of Tennessee, Civil Action No. 2:07-cv-02175-JPM, Defendants' Third Supp'l Answers & Objections to Plaintiff's First Set of Interrogatories No. 1-6, Oct. 15, 2007.

In the United States Patent and Trademark Office, in Re. U.S. Appl. No. 10/070,823, filed Jul. 15, 2002, Notice of Allowance, dated Jul. 13, 2006.

In the United States Patent and Trademark Office, in Re. U.S. Appl. No. 10/318,078, filed Dec. 13, 2002, Issue Notice, dated Mar. 28, 200.

In the United States Patent and Trademark Office, in Re. U.S. Appl. No. 10/622,535, filed Jul. 21, 2003: Notice of Allowance, dated Nov. 17, 2009.

In the United States Patent and Trademark Office, in Re. U.S. Appl. No. 10/622,535, filed Jul. 21, 2003: Non Final Office Action, dated Sep. 12, 2007.

In the United States Patent and Trademark Office, in Re. U.S. Appl. No. 11/512,327, filed Aug. 30, 2006: Notice of Allowance, dated Oct. 8, 2009.

In the United States Patent and Trademark Office, in Re. U.S. Appl. No. 10/622,535, filed Jul. 21, 2003: Non final office action dated Jan. 31, 2008.

In the United States Patent and Trademark Office, in Re. U.S. Appl. No. 10/622,535, filed Jul. 21, 2003: Non final office action dated Apr. 26, 2007.

In the United States Patent and Trademark Office, in Re. U.S. Appl. No. 10/622,535, filed Jul. 21, 2003: Non final office action dated Nov. 8, 2006.

In the United States Patent and Trademark Office, in Re. U.S. Appl. No. 10/622,535, filed Jul. 21, 2003: final rejection dated May 23, 2006.

In the United States Patent and Trademark Office, in Re. U.S. Appl. No. 10/622,535, filed Jul. 21, 2003: Non final office action dated Aug. 30, 2005.

In the United States Patent and Trademark Office, in Re. U.S. Appl. No. 10/070,823, Final rejection dated Aug. 23, 2005.

In the United States Patent and Trademark Office, in Re. U.S. Appl. No. 10/070,823, Non-final office action dated Sep. 23, 2004.

In the United States Patent and Trademark Office, in Re. U.S. Appl. No. 10/318,078, Final rejection dated Aug. 1, 2006.

In the United States Patent and Trademark Office, in Re. U.S. Appl. No. 10/318,078, Final rejection dated Nov. 12, 2004.

In the United States Patent and Trademark Office, in Re. U.S. Appl. No. 10/318,078, Non-final office action dated Apr. 21, 2004.

In the United States Patent and Trademark Office, in Re. U.S. Appl. No. 10/318,078, Non-final office action dated Aug. 8, 2005.

In the United States Patent and Trademark Office, in Re. U.S. Appl. No. 10/318,078, Notice of Allowability dated Feb. 26, 2007.

In the United States Patent and Trademark Office, in Re. U.S. Appl. No. 11/512,327, Final rejection dated Jun. 23, 2009.

In the United States Patent and Trademark Office, in Re. U.S. Appl. No. 11/512,327, Nonfinal rejection dated Oct. 6, 2008.

In the United States Patent and Trademark Office, in Re. U.S. Appl. No. 10/622,535, filed Jul. 21, 2003: Notice of Allowance dated Jul. 20, 2009.

In the United States Patent and Trademark Office, in Re. U.S. Appl. No. 10/622,535, filed Jul. 21, 2003: Non final office action dated Feb. 6, 2009.

* cited by examiner

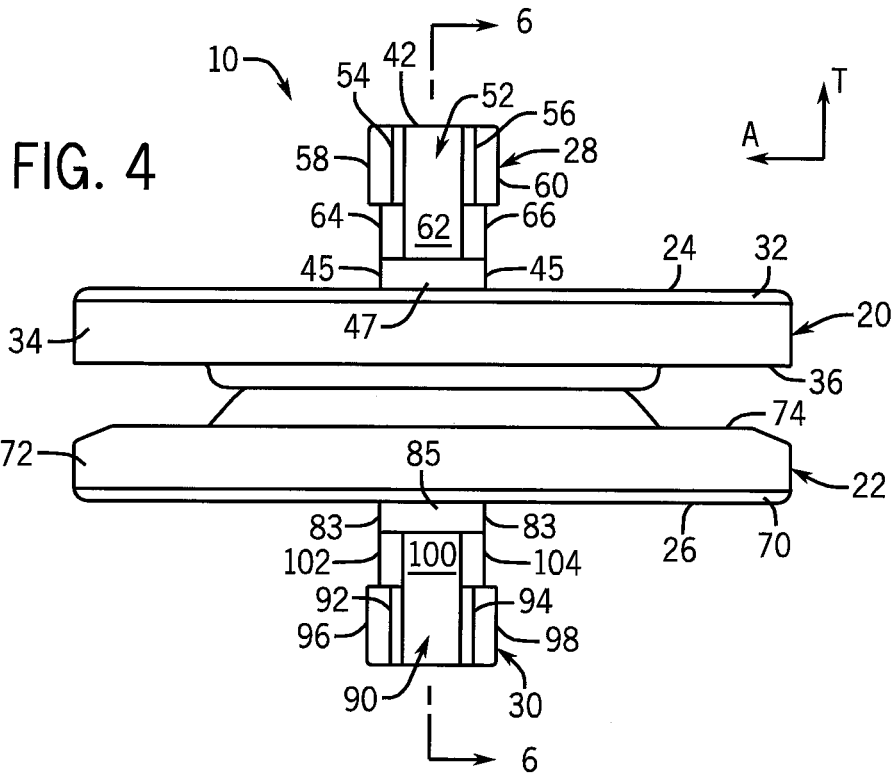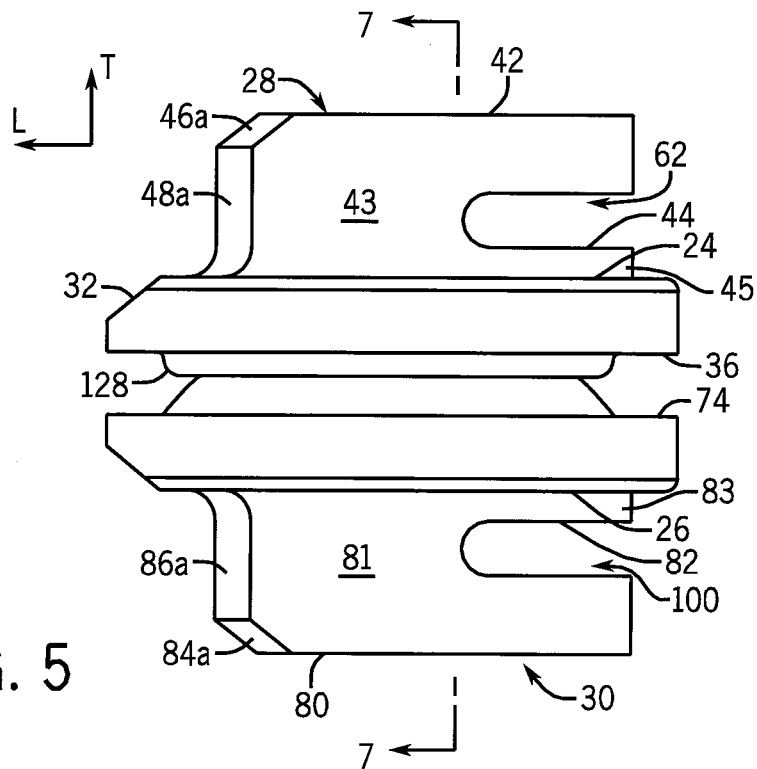

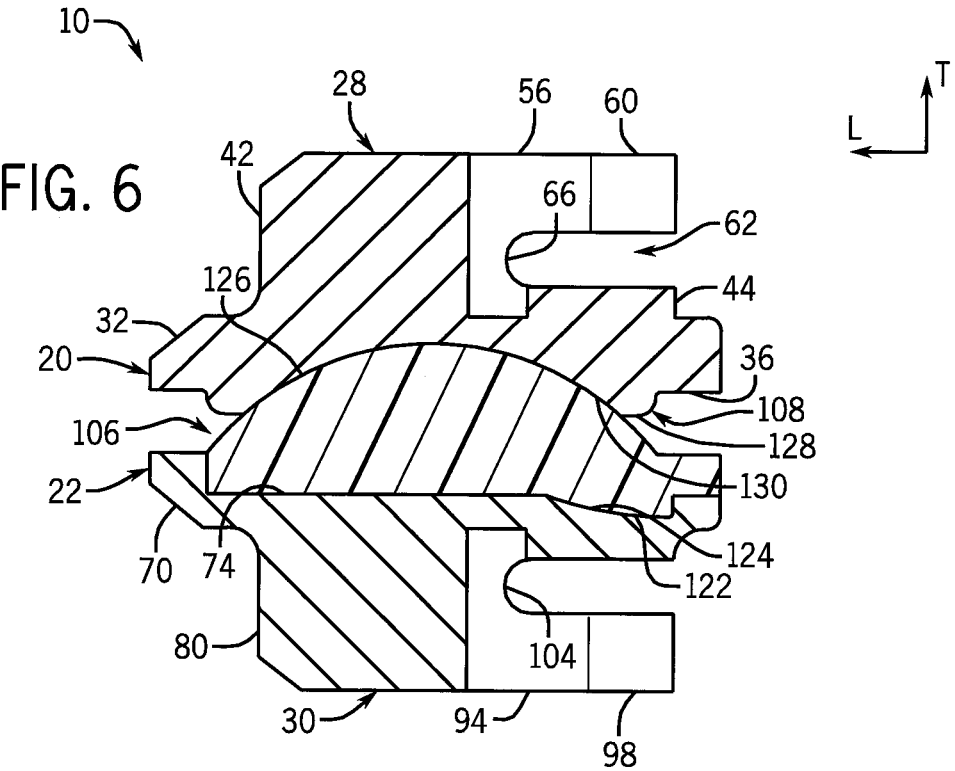
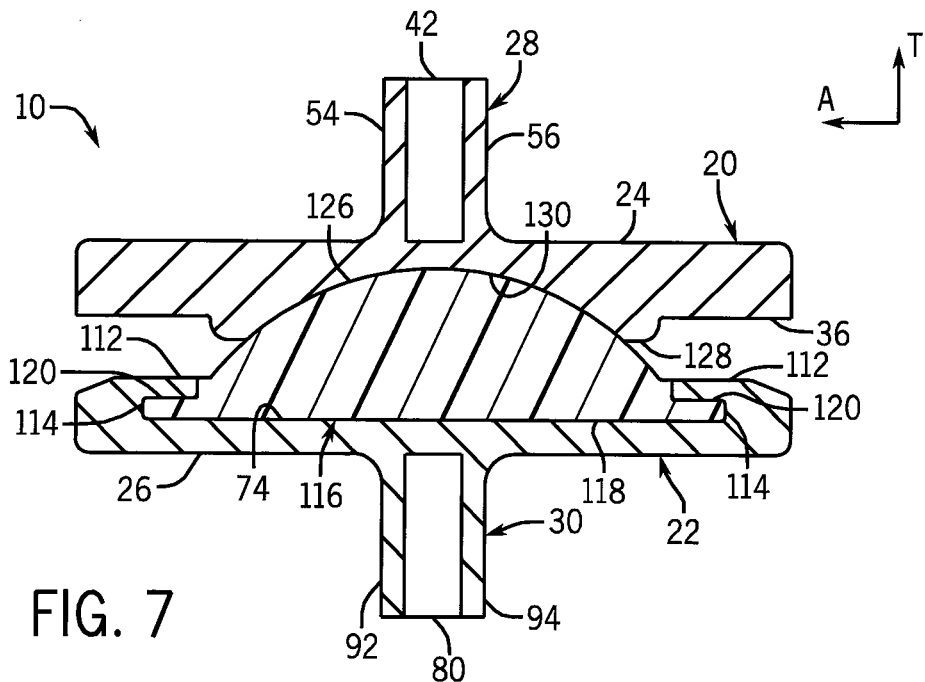

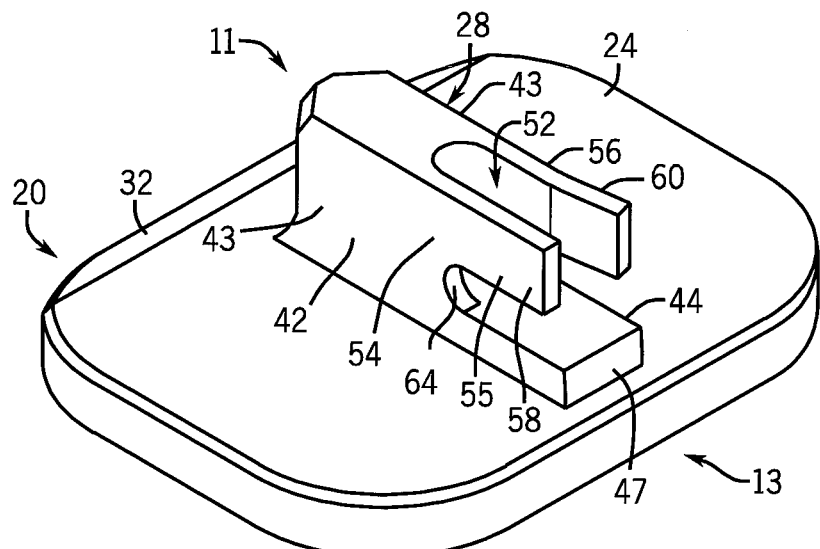
FIG. 11A
FIG. 11B
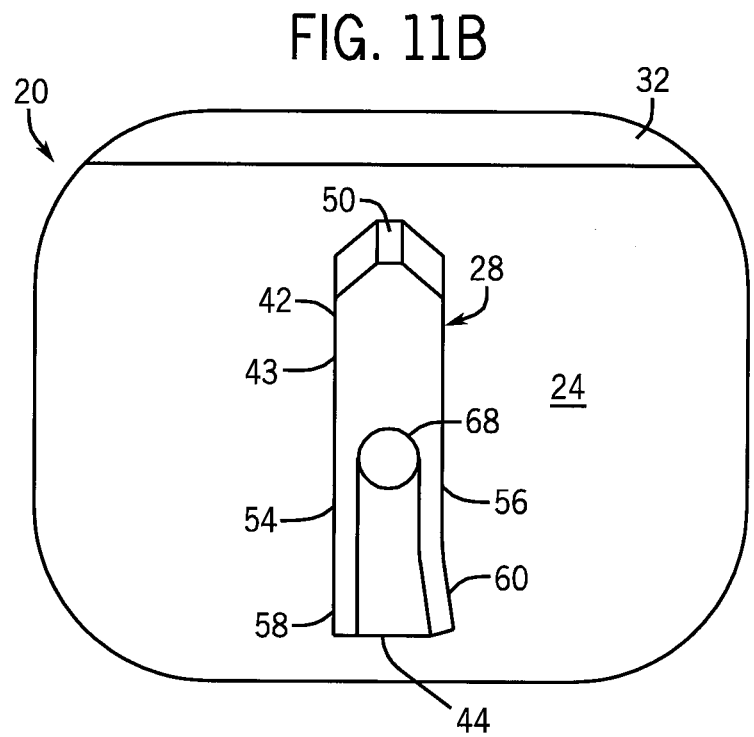

ORTHOPEDIC IMPLANT WITH FLEXIBLE KEEL

CROSS-REFERENCE TO RELATED APPLICATIONS

This claims priority to U.S. Patent Application Ser. No. 61/139,964 filed on Dec. 22, 2008, the disclosure of which is hereby incorporate by reference as if set forth in its entirety herein.

BACKGROUND

Historically, complete removal of a disc from between adjacent vertebrae resulted in fusing the adjacent vertebrae together. This "spinal fusion" procedure, which is still in use today, is a widely accepted surgical treatment for symptomatic lumbar and cervical degenerative disc disease. More recently, disc arthoplasty may be utilized to insert an artificial intervertebral disc implant into the intervertebral space between adjacent vertebrae. Such a disc implant allows limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. Sagittal balance is defined as the equilibrium of the trunk with the legs and pelvis to maintain harmonious sagittal curves and thus the damping effect of the spine. In contrast with fusion techniques, total disc replacement preserves mobility in the motion segment and attempts to mimic physiologic conditions.

One such intervertebral implant includes an upper part mounted to an adjacent vertebra, a lower part mounted to another adjacent vertebra, and an insert located between these two parts. An example of such a total disc replacement intervertebral implant is shown in U.S. Pat. No. 6,936,071, titled "Intervertebral Implant", the contents of which are incorporated herein by reference in their entirety. To provide an anchor to mount the upper and lower parts to the adjacent vertebrae, each part includes a vertically extending keel. While this and other known implants represent improvements in the art of artificial intervertebral implants, there exists a continuing need for improvements of these types of implants. Namely, it is desirable to provide bone-anchoring keels for use with orthopedic implants, such as total disc replacement implants, that are adapted for revision or explantation procedures.

SUMMARY

In accordance with one aspect, an orthopedic implant is configured to be anchored into boney tissue. The implant includes an endplate configured to be inserted into the boney tissue along a longitudinal forward direction. The endplate presents a bone contacting surface, and a keel extending out from the bone contacting surface and configured to be disposed into a slot formed into the boney tissue. The keel includes a keel body and a wing extending rearward from the keel body, the wing including a flared portion that projects laterally outward with respect to a longitudinally rearward direction. The flared portion is spaced from the bone contacting surface by a void.

BRIEF DESCRIPTION OF THE DRAWINGS

The foregoing summary, as well as the following detailed description of a preferred embodiment of the application, will be better understood when read in conjunction with the appended drawings. For the purposes of illustrating the flexible anchoring keel and related instruments of the present application, there is shown in the drawings a preferred embodiment. It should be understood, however, that the application is not limited to the precise arrangements and instrumentalities shown. In the drawings:

FIG. 4 is a front elevation view of the implant illustrated in FIG. 2;

FIG. 5 is a side elevation view of the implant illustrated in FIG. 2;

FIG. 6 is a cross-sectional view of the implant illustrated in FIG. 4, taken along line 6-6

FIG. 7 is a cross-sectional view of the implant illustrated in FIG. 5, taken along line 7-7;

FIG. 11A is a perspective view of an intervertebral implant constructed in accordance with another alternative embodiment;

FIG. 11B is a top plan view the intervertebral implant illustrated in FIG. 11A;

DETAILED DESCRIPTION

Figure 1A:
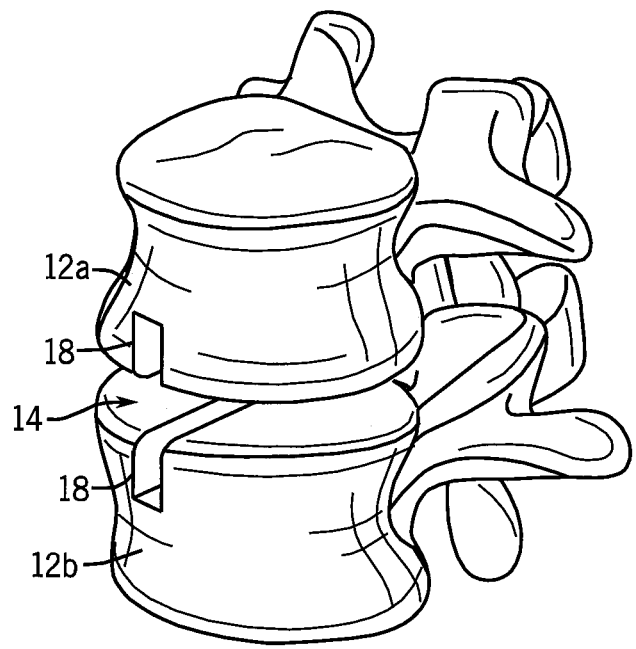
FIG. 1A is a perspective view of a pair of vertebral bodies separated by an intervertebral space, wherein each of the vertebral bodies has keel slots formed therein.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the implant assembly and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Figure 1B:
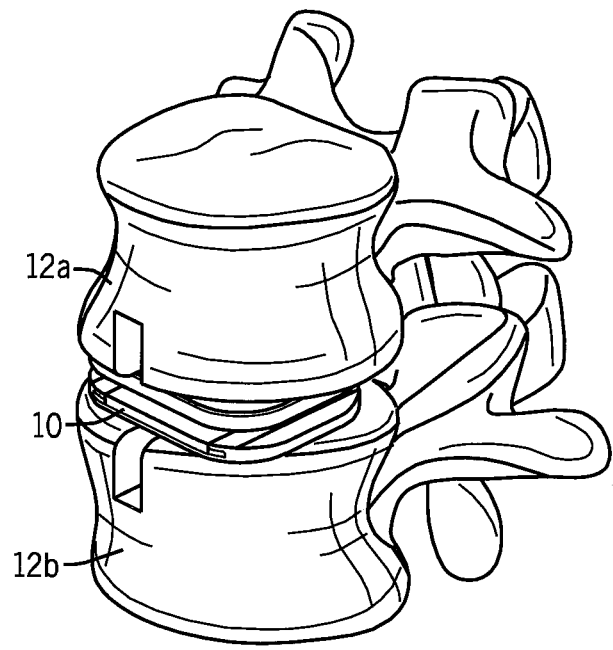
FIG. 1B is a perspective view of the vertebral bodies illustrated in FIG. 1, and an intervertebral implant inserted into the intervertebral space between the two vertebral bodies.
Figure 2:
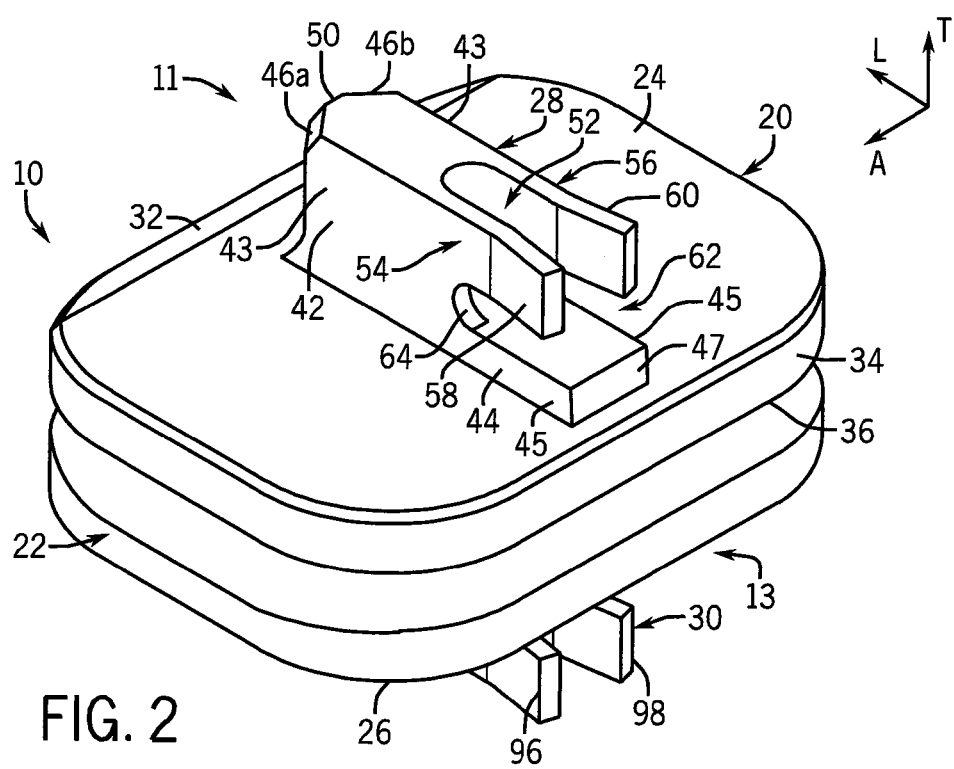
FIG. 2 is a perspective view of an intervertebral implant illustrated in FIG. 1B, and constructed in accordance with one embodiment including first and second endplates.
Figure 3A:
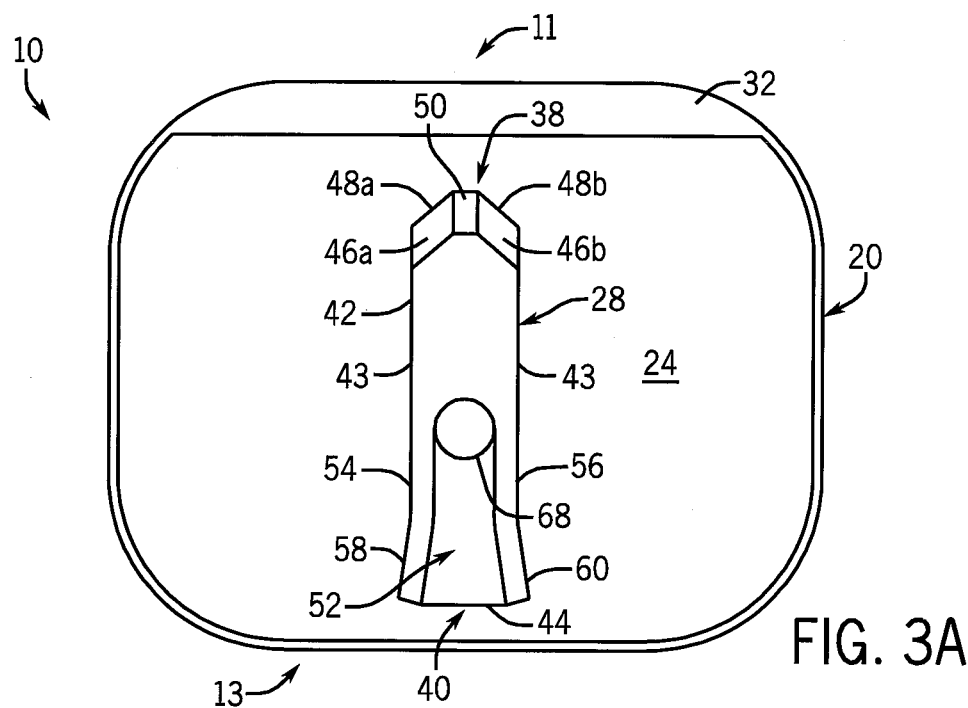
FIG. 3A is a top plan view of the implant illustrated in FIG. 2.
Figure 3B:
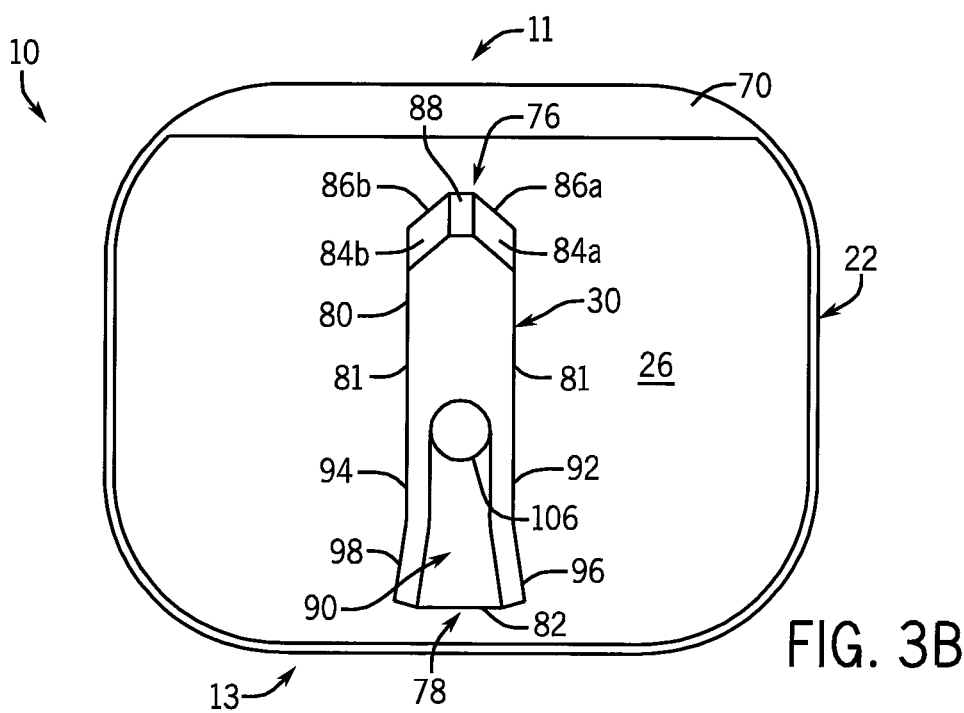
FIG. 3B is a bottom plan view of the implant illustrated in FIG. 2.

Referring to FIGS. 1A-2, a pair of adjacent vertebral bodies 12, including a superior vertebral body 12a and an inferior vertebral body 12b, defines an intervertebral space 14 disposed therebetween. As illustrated, the intervertebral space 14 is illustrated after a discectomy, whereby the disc material has been removed to prepare the intervertebral space 14 to receive an implant, such as the intervertebral implant 10 illustrated in FIG. 2. Thus, the implant 10 is configured to be inserted into the intervertebral space 14, and achieve improved stability between the vertebral bodies 12 (for fusion or non-fusion procedures). The intervertebral space 14 can be disposed anywhere along the spine, but is disposed in the cervical region of the spine in accordance with one embodiment.

The implant 10 and various components of the implant are described herein extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components.

It should be appreciated that while the longitudinal and lateral directions are illustrated as extending along a horizontal plane, and that the transverse direction is illustrated as extending along a vertical plane, the planes that encompass the various directions may differ during use. Accordingly, the directional terms "vertical" and "horizontal" are used to describe the implant 10 and its components as illustrated merely for the purposes of clarity and illustration.

In the illustrated embodiment, the longitudinal direction L extends in an anterior-posterior direction, the lateral direction A extends in a medial-lateral direction, and the transverse direction T extends in a caudal-cranial direction. It should be appreciated, however, that the various directions defined by the implant 10 could alternatively be oriented at any desirable angle between 0° and 180° with respect to the medial-lateral and anterior-posterior directions and the transverse direction.

Referring now to FIGS. 1-7 generally, the implant 10 generally includes a first, or upper, endplate 20 and a second, or lower, endplate 22. The endplates 20 and 22, and components thereof, can be formed from a variety of biocompatible materials, such as cobalt chromium molybdenum (CoCrMo) with a porous plasma-sprayed titanium coating, titanium, stainless steel, ceramics, or polymers such as polyetheretherketone (PEEK). The endplates 20 and 22 define substantially planar outer transverse bone-contacting surfaces 24 and 26, respectively, and respective flexible keels 28 and 30 extending transversely out from the surfaces 24 and 26. In the illustrated embodiment, the keels 28 and 30 are perpendicular with respect to the surfaces 24 and 26. The surfaces 24 and 26 can be smooth or textured to facilitate fusion with the associated vertebral body 12. The implant 10 defines a longitudinally forward end 11 and a longitudinally rear end 13 with respect to the direction of insertion of the implant 10 into the intervertebral space 14. Thus, the implant 10 is configured to be inserted into the intervertebral space 14 along the forward longitudinal direction that extends from the rear end 13 toward the front end 11. Thus, the terms "forward" and "rearward" and derivatives thereof, as used herein with respect to the components of the implant 10, are used reference to the forward and rear ends 11 and 13 of the implant 10.

In order to position implant 10 into the intervertebral disc space 14, a cut is made in the inferior as well as in the superior vertebral bodies 12 to provide keel cuts or slots 18 that extend therein that conform generally to the size and shape of the keels 28 and 30. The keel cuts or slots 18 can be provided using any method and apparatus as desired, such as a chisel or a drilling/milling system of the type disclosed in U.S. patent application Ser. No. 12/375,710, filed Jan. 30, 2009, the disclosure of which is hereby incorporated by reference as if set forth in its entirety herein. It should be appreciated that the slots 18 are formed in vertebral bodies 12a-b, the slots can alternatively be disposed in boney tissue associated with any bone in the human body as desired, unless otherwise indicated.

The implant 10 can further include a plastic insert, or inlay 116 connected to the lower endplate 22 and disposed between the lower endplate 22 and the upper endplate 20. The implant 10 can define a width extending along the lateral direction A that can be between approximately 15-19 mm, a length extending along the longitudinal dimension L that can be approximately 12-16 mm, and a height extending between the outer surfaces 24 and 26 along the transverse direction T that can be approximately 5-9 mm. Thus, the implant 10 is suitable for implantation in an intervertebral space in the cervical region of the spine, which is characterized by the need for precision because of the relatively small dimensions of cervical intervertebral spaces.

The dimensions described above with respect to the implant 10 in the illustrated embodiment are in contrast to the dimensions of the implant 10 if the implant were to be inserted into an intervertebral space in the a different spinal region, for instance the lumbar region. The implant 10 configured for implantation into the lumbar region can have a width between approximately 27 and 30 mm, a length of approximately 34-39 mm, and a height of approximately 10-14 mm.

It is to be understood that the implant 10 can be constructed with any dimensions desirable for implantation of any intervertebral space along the spine, and is not limited to the cervical and lumbar regions unless otherwise indicated. Furthermore, while the implant 100 is configured as a total disc replacement device, implants constructed in accordance with the teachings described herein are readily configurable for use with a range of bone-anchored orthopedic prostheses, such as interbody spacers, hip and knee replacement implants, and the like.

The first endplate 20 will now be described with particular reference to FIGS. 2A-5. It should be appreciated that the directions "transversely in" and "transversely out" and derivatives thereof are used with respect to the first endplate 20 to describe upward and lower directions, respectively, when the endplate 20 is provided as an upper endplate as illustrated. In particular, the upper endplate 20 defines the outer surface 24 that engages and supports the superior vertebral body 12a. The outer surface 24 is bound by edges 32 that are slightly beveled all the way around with the largest portion of the bevel being at the forward end 11 of the implant 10. The endplate 20 includes a peripheral side wall 34 that projects transversely in from the beveled edges 32, and an inner transverse surface 36 positioned such that the side wall 34 extends between the outer surface 24 and the inner surface 36.

The keel 28 can be integrally connected to the outer surface 24 of the upper endplate 20, and sized and configured to be inserted into the slot 18 formed in one of the vertebral bodies 12, such as the superior vertebral body 12a. In this regard, the keel 28 can be construed as an anchoring keel configured to be disposed in the slot 18. The slot 18 can be pre-formed in the manner described above, or can be cut while inserting the keel 28 into the vertebral body. While the upper endplate 20 is illustrated as being associated with the superior vertebral body 12a, and the lower endplate 22 is described as being associated with the inferior vertebral body 12b, it should be appreciated that the endplate 20 can alternatively be attached to the inferior vertebral body 12b, and the lower endplate 22 can alternatively be attached to the superior vertebral body 12a, depending on the orientation of the implant 10.

The keel 28 defines a proximal end 38 disposed proximate to the forward end 11 of the implant 10, and a distal end 40 disposed proximate to the rear end 13 of the implant 10. The keel 28 includes a keel body 42 and a base 44. The keel body 42 is spaced transversely out from the outer surface 24. In particular, the keel body 42 extends transversely out from a base 44 that is integrally connected to, and extends transversely out from, the outer surface 24. The keel body 42 defines a pair of opposing side walls 43 that extend transversely out from the base 44, and can be co-planar with opposing side walls 45 of the base 44. The base 44 further includes a distal engagement surface 47 that extends transversely out from the outer transverse surface 24, and extends laterally between the distal, or rear, ends of the side walls 45.

The proximal end of the keel 28 includes a pair of v-shaped upper bevels 46a-b and a pair of v-shaped vertical beveled surfaces 48a-b extending transversely in from the upper bevels 46a-b. The bevels 46a and 48a are spaced from each other by the bevels 46b and 48b by a substantially flat, laterally extending, front surface 50. The bevels 46, 48, and the front surface 50 define a front keel profile that is substantially "arrow" shaped. The "arrow" shape facilitates insertion of the keel 28 into the slot 18 formed in the corresponding vertebral body 12a.

A first aperture 52 extends transversely into the distal end of the keel body 42 and terminates at the base 44. The aperture 52 is longitudinally elongated, and extends distally through the body 42, such that the distal end of the body 42 is open. The aperture 52 defines a first wing 54 and a second wing 56 of the keel 28. The first and second wings 54 and 56 extend rearward from the keel body 42. The second wing 56 is laterally spaced from the first wing 54 via the aperture 52. The wings 54 and 56 are laterally spaced from each other by the aperture 52, which provides a void that separates the wings 54 and 56. Each wing 54 and 56 can be flexible as illustrated and configured to move with respect to the outer transverse surface 24. In accordance with the illustrated embodiment, each wing 54 and 56 terminates at its distal end at a first flexible flared distal region 58 and a second flexible flared distal region 60, respectively. The flared regions 58 and 60 project laterally outward with respect to the side walls 43 in a distal, or rearward, direction along the flared regions 58 and 60.

A channel 62 extends longitudinally forward from the distal end of the keel 28 at a location transversely between the base 44 and the wings 54 and 56. The channel 62 extends longitudinally into, but not longitudinally through, the keel 28 and terminates at a distance that is distal with respect to the longitudinal boundary of the aperture 52. The channel 62 further extends laterally through the keel 28. Accordingly, the wings 54 and 56, including the flared regions 58 and 60, are transversely spaced from the base 44 and the outer transverse surface 24 by channel 62. The channel 62 thus defines a void that separates the wings 54 and 56 from the base 44 and the outer surface 24. The wings 54 and 56 are thus spaced from the base 44, or suspended above the base 44 when the first endplate 20 engages the superior vertebral body 12a, but could be suspended below the base 44 if the first endplate 20 engages the inferior vertebral body 12b.

The keel 28 thus defines a pair of distally-facing surfaces 64 and 66, respectively, extending transversely between the base 44 and the wings 54 and 56. If desired, the engagement surfaces 64 and 66 can be curved along the transverse direction as illustrated. The keel 28 can further include a an instrument engagement feature in the form of a recess 68 protruding transversely into the base 44 at a location between the wings 54 and 56, such that the recess 68 is accessible through the aperture 52.

The second endplate 22 will now be described with continuing reference to FIGS. 2A-5. It should be appreciated that the directions "transversely in" and "transversely out" and derivatives thereof are used with respect to the second endplate 22 to describe lower and upper directions, respectively, when the endplate 22 is provided as a lower endplate as illustrated. In particular, the lower endplate 22 defines the outer surface 26 that engages and supports the inferior vertebral body 12b. It will be appreciated that the second endplate 22 is constructed substantially as described with respect to the first endplate 20, such that the structural features extending transversely out from the outer transverse surface 26 of the second endplate 22 are aligned with like structural features that extend transversely out from outer the transverse surface 24 of the first endplate 20.

The outer surface 26 is bound by edges 70 that are slightly beveled all the way around with the largest portion of the bevel being at the forward end 11 of the implant 10. The endplate 22 includes a peripheral side wall 72 that projects transversely in from the beveled edges 70, and an inner transverse surface 74 positioned such that the side wall 72 extends between the outer surface 26 and the inner surface 74.

The keel 30 can be integrally connected to the outer surface 26 of the second endplate 22, and sized and configured to be inserted into the slot 18 formed in one of the vertebral bodies 12, such as the inferior vertebral body 12b. The slot 18 can be pre-formed in the manner described above, or can be cut while inserting the keel 30 into the vertebral body. While the lower endplate 22 is illustrated as being associated with the inferior vertebral body 12b, and the upper endplate 20 is described as being associated with the superior vertebral body 12a, it should be appreciated that the endplate 22 can alternatively be attached to the superior vertebral body 12a, and the upper endplate 20 can alternatively be attached to the inferior vertebral body 12b, depending on the orientation of the implant 10.

The keel 30 defines a proximal end 76 disposed proximate to the forward end 11 of the implant 10, and a distal end 78 disposed proximate to the rear end 13 of the implant 10. The keel 30 includes a keel body 80 spaced transversely out from the outer surface 26. In particular, the keel body 80 extends transversely out from a base 82 that is integrally connected to, and extends transversely out from, the outer surface 26. The keel body 80 defines a pair of opposing side walls 81 that extend out from the base 82, and can be co-planar with opposing side walls 83 of the base 82. The base 82 further includes a distal engagement surface 85 that extends transversely out from the outer transverse surface 26, and further extends laterally between the distal, or rear, ends of the side walls 83.

The proximal end 76 of the keel 30 includes a pair of v-shaped upper bevels 84a-b and a pair of v-shaped vertical beveled surfaces 86a-b extending transversely in from the upper bevels 84a-b. The bevels 84a and 86a are spaced by the bevels 84b and 86b by a substantially flat, laterally extending, front surface 88. The bevels 84, 86, and the front surface 88 define a front keel profile that is substantially "arrow" shaped. The "arrow" shape facilitates insertion of the keel 20 into the slot 18 formed in the corresponding vertebral body 12b.

A first aperture 90 extends transversely into the distal end 78 of the keel body 80 and terminates at the base 82. The aperture 90 is longitudinally elongated, and extends distally through the body 80, such that the distal end of the body 42 is open and defines a first wing 92 and a second wing 94 disposed at the distal end 78 of the keel 30. The first and second wings 92 and 94 extend rearward from the keel body 80. The wings 92 and 94 are laterally spaced from each other by the aperture 90, which provides a void that separates the wings 92 and 94. Each wing 92 and 94 can be flexible as illustrated and configured to move with respect to the outer transverse surface 26. In accordance with the illustrated embodiment, each wing 92 and 94 terminates at its distal end at a first flexible flared region 96 and a second flexible flared region 98, respectively. The flared regions 96 and 98 project laterally outward with respect to the side walls 81 in a distal, or rearward, direction along the flared regions 96 and 98, respectively.

A channel 100 extends longitudinally forward from the distal end of the keel 30 at a location transversely between the base 82 and the wings 92 and 94. The channel 100 extends longitudinally into, but not longitudinally through, the keel 30 and terminates at a distance that is distal with respect to the longitudinal boundary of the aperture 90. The channel 100 further extends laterally through the keel 30. Accordingly, the wings 92 and 94, including the flared regions 96 and 98, are spaced from the base 82 and the outer transverse surface 26 by the channel 100. The channel 100 thus defines a void that separates the wings 92 and 94 from the base 44 and the outer surface 24. The wings 92 and 94 are thus suspended below the base 82 when the second endplate 22 engages the inferior vertebral body 12b, but could be suspended above the base 82 if the second endplate 22 engages the superior vertebral body 12a.

The keel 30 thus defines a pair of distally-facing surfaces 102 and 104, respectively, extending transversely between the base 82 and the wings 92 and 94. If desired, the surfaces 102 and 104 can be curved along the transverse direction as illustrated. The keel 30 can further include an instrument engagement feature in the form of a recess 106 protruding transversely into the base 82 at a location between the wings 92 and 94, such that the recess 106 is accessible through the aperture 90.

Referring now to FIGS. 4-7, the endplates 20 and 22 are mated at a joint 106 that is provided as an articulating joint configured to pivot each endplate 20 and 22 relative to the other endplate universally about 360°. The joint 106 can be constructed as described in U.S. patent application Ser. No. 11/669,273, the disclosure of which is hereby incorporated by reference as if set forth in its entirety herein, or in accordance with any suitable alternative embodiment.

The endplates 20 and 22 thus each include respective mating joint members 108 and 110, respectively. In particular, the lower endplate 22 includes a pair of C-shaped support members 112 that extend transversely inwardly from the inner surface 74. The support members 112 present laterally inwardly facing receiving channels 114 that are configured to receive a plastic inlay 116. The inlay 116 includes a base 118 having laterally outer ends 120 that are sized to fit inside the channels 114. Thus, the inlay 116 can be inserted into the channels 114 in a direction from the rear end 13 of the endplate 22 toward the front end 11 of the endplate 22. The endplate 22 can include a stop disposed at the front end 11 to prevent over-insertion of the inlay 116. The inlay 116 can include a snap-in projection 122 that engages a snap-in recess 124 extending into the inner transverse surface 74 so that the inlay 116 can snap into place to prevent inadvertent removal.

The inlay 116 further includes a dome-shape upper surface 126 centrally disposed on the base 118 and extending transversely in from the base 118. The first endplate 20 includes a raised surface 128 extending transversely in from the inner surface 36. The raised surface 128 defines a dome-shaped recess 130 projecting therein that is contoured and configured to receive and mate with the dome-shaped upper surface 126. Thus, the endplates 20 and 22 are configured to pivot universally with respect to each other about a 360° range of motion.

While the joint 106 has been described in accordance with one embodiment, it should be appreciated that the implant could include any alternatively constructed joint that enables relative motion between the endplates 20 and 22 in any direction, or that fixedly attaches the endplates 20 and 22. In this regard, it should be appreciated that the first endplate 20 could carry the inlay 116, and the second endplate 22 could carry a raised surface such as raised surface 128 that engages the inlay 116.

Figure 8:
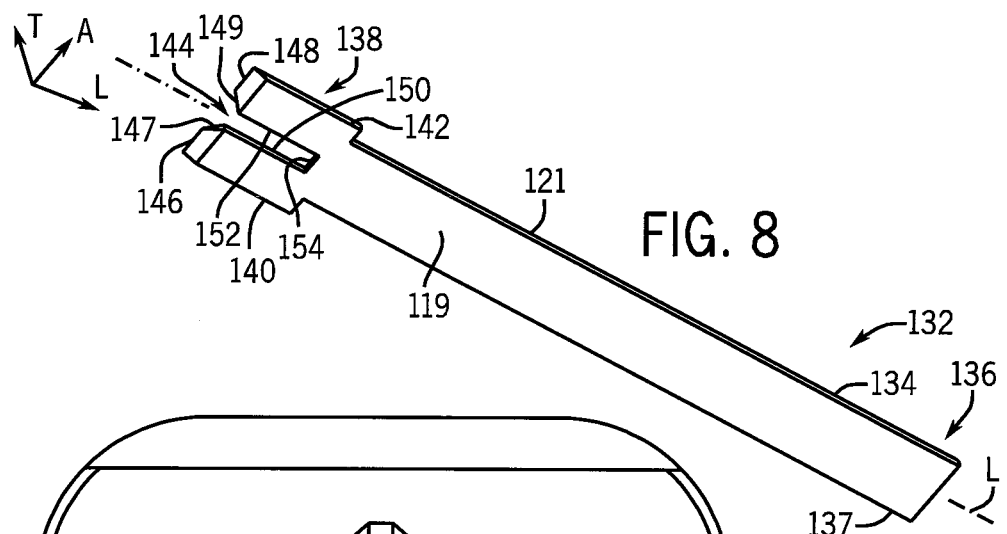
FIG. 8 is a perspective view of a forked osteotome instrument, constructed in accordance with one embodiment.

Referring now FIG. 8, a forked osteotome instrument 132 can be provided and configured to insert one or both of the endplates 20 and 22 into the intervertebral space 14 described above. Because the keels 28 and 30 are substantially identically constructed, the instrument 132 is described herein as engaging the keel 28 of the first endplate 20, it being appreciated that the description applies to the engagement of the instrument with the second endplate 22. In this regard, it should be further appreciated that a pair of instruments 132 can be provided to engage the upper and lower endplates 20 and 22, or that a single instrument can be provided having a pair of transversely spaced arms 140 and 142 that are configured to engage the keels 28 and 30 of both endplates 20 and 22, respectively.

The instrument 132 includes a shaft 134 that is elongated along a longitudinal axis L, and defines a proximal end 136 that defines a handle 137, and an opposing distal end 138. The instrument further defines a first, or outer transverse, surface 119, and a second, or inner transverse, surface 121 opposite the first surface 119. The instrument 132 includes a first arm 140 and a second arm 142 that extend distally from the shaft 134. The arms 140 and 142 are spaced laterally (or horizontally) by a gap 144, such that the instrument defines a forked distal end 138. Each arm 140 and 142 can define a distal edge 146 and 148, respectively, that is beveled or flared longitudinally rearward in the transverse direction. In particular, the distal edges 146 and 148 are beveled in a transverse direction from the inner transverse surface 121 to the outer transverse surface 119 along the edges 146 and 148 from the distal end 138 toward the proximal end 136. The beveled edges 146 and 148 can assist when inserting the implant 10 into the intervertebral space 14. The instrument 132 defines longitudinally extending, and laterally opposing, inner guide surfaces 150 and 152 of the arms 140 and 142, respectively, and an inner stop surface 154 that extends laterally between the arms 140 and 142.

In the illustrated embodiment, the distal edges 146 and 148 present laterally inner surfaces 147 and 149, respectively, that are beveled or flared laterally outward with respect to the inner guide surfaces 150 and 152 along a longitudinal direction from the proximal end 136 toward the distal end 138. Thus, the distal edges 146 and 148 define a lateral width therebetween that is greater than the lateral width disposed between the inner guide surfaces 150 and 152. The width disposed between the arms 140 and 142 thus tapers outwardly, with respect to the longitudinal axis L, at the distal end 138 of the instrument 132. The tapered width facilitates engagement of the instrument 132 with the endplate 20.

Referring now to FIGS. 2 and 8, the gap 144 has a lateral dimension substantially equal to, or slightly greater than, the lateral width that separates the opposing side walls 43 of the keel body 42, and thus also has a lateral dimension substantially equal to, or slightly greater than, the lateral width that separates the opposing side walls 45 of the keel body 42. Otherwise stated, the inner stop surface 154 has a lateral dimension substantially equal to, or slightly greater than, the lateral width that separates the opposing side walls 43 of the keel body 42, and thus also has a lateral dimension substantially equal to, or slightly greater than, the lateral width that separates the opposing side walls 45 of the keel body 42

At least a portion of the instrument 132 that engages the keel 28, for instance a portion of the arms 140 and 142 and/or the shaft 134, defines a height that can be substantially equal to the transverse height of the base 44, or the engagement surface 47 (or the transverse distance between the outer transverse surface 24 of the endplate 20 and the outer transverse surface of the base 44 or engagement surface 47). Alternatively, the height can be greater than or less than the height of the base 44 or engagement surface 47, such that the arms 140 and 142 are configured to engage the keel 28 during operation.

In accordance with an alternative embodiment, the height of the portion of the instrument 132 that engages the keel can have a height that is substantially equal to, or slightly less than, the transverse distance between the base 44 and the wing 54 and 56. Otherwise stated, the height of the portion of the instrument 132 that engages the keel 28 can be configured to fit within the channel 62. Alternatively, if it is desired to prevent the instrument 132 from being inserted into the channel 62, the inner stop surface 154 can have a height greater than that of the channel 62.

Figure 9A:
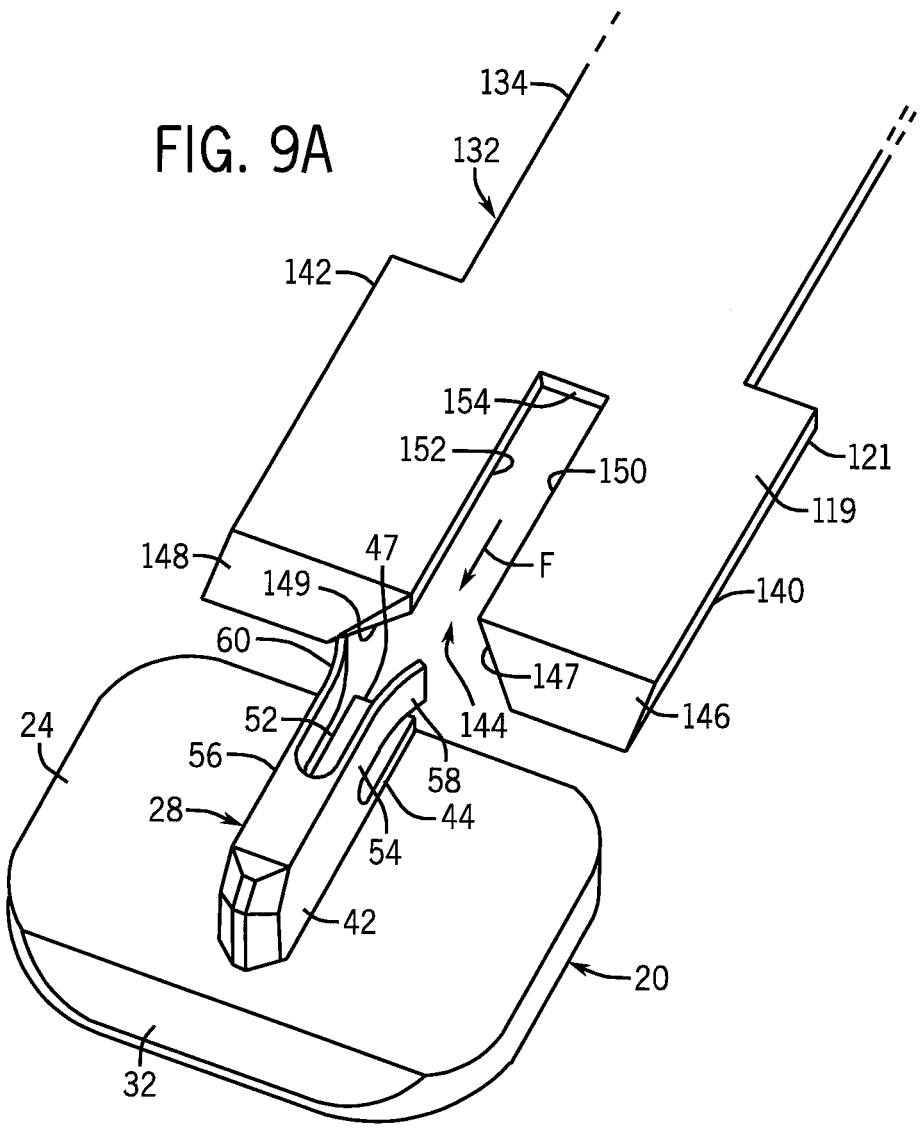
FIGS. 9A-B are perspective views of the forked osteotome instrument illustrated in FIG. 8 coupled to the first implant endplate illustrated in FIG. 2.
Figure 9B:
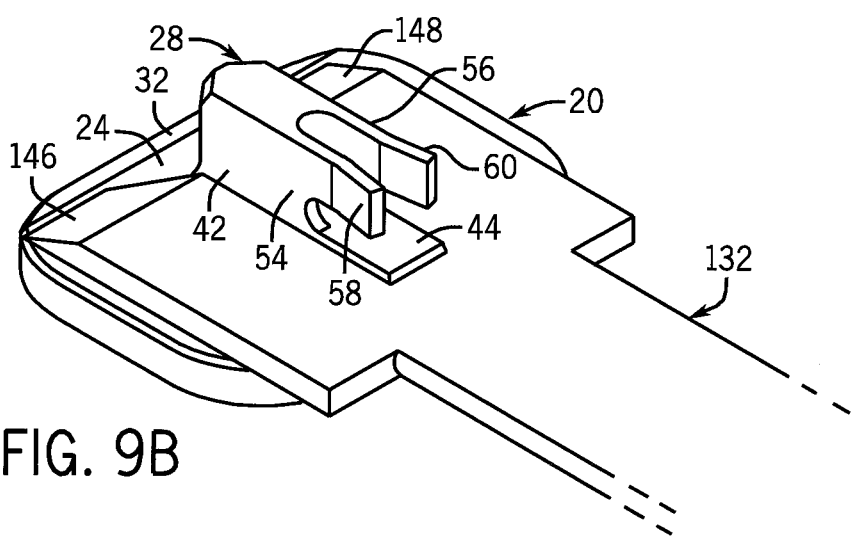

Referring now to FIGS. 9A-B, the instrument 132 engages the keel 28 of the endplate 20 in order to facilitate insertion of the endplate 20 into the intervertebral space 14. In particular, the instrument 132 is oriented such that the second surface 121 is positioned to rest against the outer transverse surface 24 of the endplate 20. The instrument 132 is positioned such that the gap 144 separating the arms 140 and 142 is aligned with the engagement surface 47 of the base 44. The instrument 132 can be oriented such that the inner transverse surface 121 is generally aligned with the engagement surface 47.

The instrument 132 can then be translated with respect to the endplate 20 in the longitudinally forward direction indicated by arrow F, such that the gap 144 receives the base 44 therein. The beveled surfaces 147 and 149 can correct any slight misalignments between the gap 144 and the base 44 during insertion. Thus, as the instrument 132 engages the endplate 20, the inner surfaces 150 and 152 of the arms 140 and 142 ride along the side walls 45 of the base 44 until the base 44 is captured between the arms 140 and 142. The instrument 132 is translated longitudinally forward to a fully mated position with the keel 28, whereby the stop surface 154 abuts the engagement surface 47. Continued forward motion of the instrument 132 then translates the endplate 20 into the intervertebral space 14. Thus, the engagement surface 47 is configured to abut the stop surface 154 and receive a longitudinally forward biasing force from the stop surface 154 that biases the endplate in the longitudinally forward direction.

When the instrument 132 and the endplate 20 are fully mated, the beveled edges 146 and 148 flare transversely out from the outer transverse surface 24, and thus assist when inserting the endplate 20 into the intervertebral space 14. In one embodiment, the beveled edges 146 and 148 are disposed behind the beveled front edge 32 of the endplate 20 such that the bevel 32 first engages the intervertebral space, followed by the beveled edges 146 and 148. The bevels 32, 146, and 148, thus cooperate to facilitate insertion of the endplate 10 into the intervertebral space 14.

The wings 54 and 56, including the first and second flared regions 58 and 60, are inserted into the slot 18 formed in the vertebral body 12a, such that the flared regions 58 and 60 of the wings 54 and 56, respectively, engage the vertebral wall that defines the slot 18. Because the aperture 52 separates the flared regions 58 and 60, the flared regions 58 and 60 are flexible, and capable of flexing toward each other relative to the remainder of the endplate 20. Thus, the flared regions 58 and 60 are capable of moving with respect to the bone contacting outer transverse surface 24 and the base 44. Because the flared regions 58 and 60 are transversely spaced from the surface 24 and the base 44, the transverse inner edge of the flared regions 58 and 60 are flexible with respect to the surface 24 and the base 44. The inclusion of the flexible keel 28 may reduce the insertion force necessary to implant a device featuring the keel 28 when compared to an implant featuring a conventional, nonflexible keel. Because the flared regions 58 and 60 of the wings 54 and 56 are spaced transversely out from the base 44, interference between the insertion instrument 132 and the flared regions 58 is avoided as the endplate 20 is inserted into the intervertebral space 14.

It should be appreciated that a keel similar to the flexible keels 28 and 30 described above can alternatively be configured for use with interbody spacers or other orthopedic implants designed to be anchored to boney tissue. The alternate implants may then be revised and/or explanted using a similar method to those described above for the implant having the endplate 10 with the flexible keel 28. Thus, the implant 10 can be considered as an orthopedic implant.

Figure 10A:
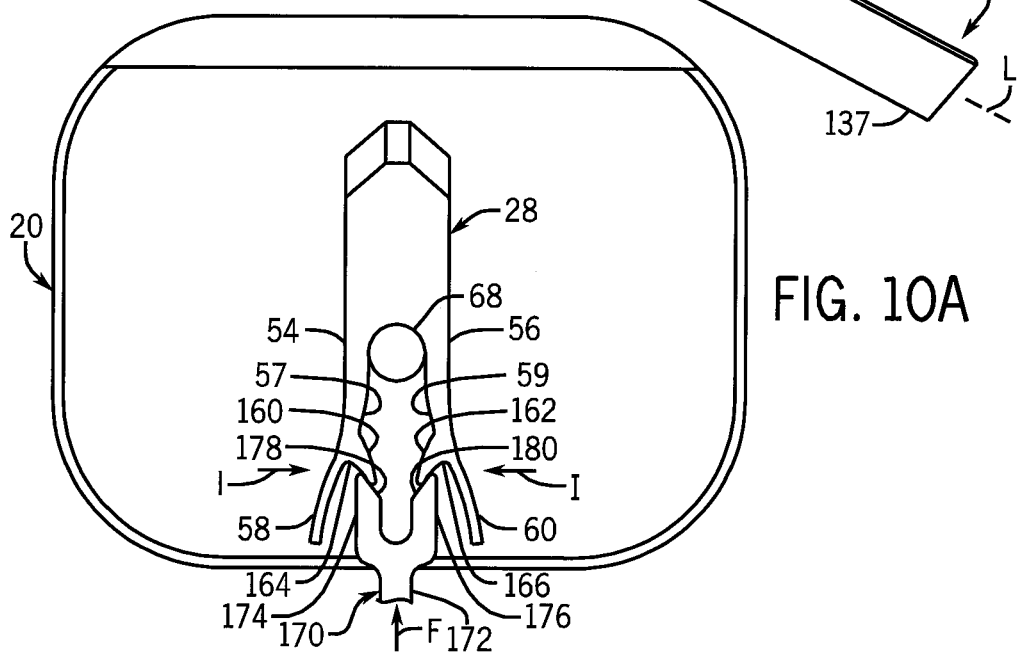
FIG. 10A is a top plan view of an intervertebral implant including a pair of endplates constructed in accordance with an alternative embodiment, showing the coupling of an osteotome instrument constructed in accordance with an alternative embodiment to one of the endplates.
Figure 10B:
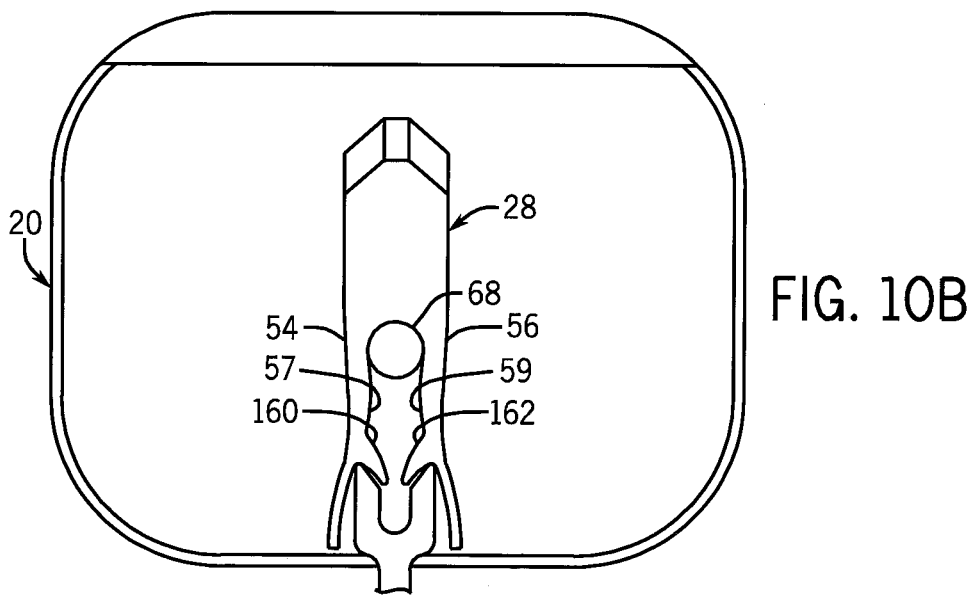
FIG. 10B is a top plan view of the intervertebral implant illustrated in FIG. 10A, showing the osteotome instrument coupled to the endplate.

Referring to FIGS. 10A-B, the endplate 20 can be constructed in accordance with an alternative embodiment so as to facilitate easy removal of the endplate 20 from the intervertebral space 14. In particular, the keel 28 includes a pair of engagement walls 160 and 162 that extend laterally inward from respective laterally inner surfaces 57 and 59 of the wings 54 and 56. The engagement walls 160 and 162 present rear engagement surfaces 164 and 166, respectively, that are angled longitudinally rearward from the inner surfaces 57 and 59 along a laterally inward direction along the surfaces 164 and 166.

A removal instrument 170 includes a shaft 172 and a pair of laterally spaced arms 174 and 176, respectively, each having a respective distal engagement surface 178 and 180. Each engagement surface 178 and 180 is angled longitudinally rearward along a laterally inward direction along the surfaces 178 and 180. Thus, the engagement surfaces 178 and 180 are configured to align and mate with the engagement surfaces 164 and 166. The arms 174 and 176 are rigid at least with respect to lateral movement, such that forward motion of the removal instrument 170 relative to the endplate 20 along the direction of Arrow F causes the engagement surfaces 170 and 180 to engage the engagement surfaces 164 and 166. Continue forward movement causes the surfaces 164 and 166 to ride laterally inward along the engagement surfaces 170 and 180. As the surfaces 164 and 166 ride along the engagement surfaces 170 and 180, the engagement surfaces 170 and 180 impart a laterally inward biasing force against the engagement surfaces 170 and 180, and thus against the corresponding flared regions 58 and 60 of the wings 54 and 56 that causes the flared regions 58 and 60 to flex or retract laterally inward toward each other along the direction of Arrow I. Thus, the engagement surfaces 164 and 166 are disposed between the flared regions 58 and 60, and are configured to receive a force from an instrument that biases the flared regions 58 and 60 toward each other.

Thus, the flared regions 58 and 60 are configured to retract from a first outer position illustrated in FIG. 10A, whereby the regions 58 and 60 are configured to abut, and engage, the surfaces of the vertebral body 12a that define the slot 18, to a second inner position illustrated in FIG. 10B, whereby the flared regions 58 and 60 are flexed laterally inward away from, and thus disengaged from, the surfaces of the vertebral body 12a that define the slot 18. Accordingly, the flared regions 58 and 60 can be disengaged from the vertebral surfaces to facilitate revision and/or explantation of the endplate 20.

It should be appreciated that the second endplate 22 can be constructed substantially as described above with respect to the endplate 20. Accordingly, the second endplate can include engagement walls as described with respect to the engagement walls 160 and 162 extending from the laterally inner surfaces of the wings 92 and 94 in the manner described above.

It should be appreciated that the keels 28 and 30 have been described in accordance with certain embodiments, and that the keels 28 and 30 can be constructed in accordance with any alternative embodiment, such that at least one or both of the keels 28 and 30 includes a flexible and/or flared wing. For instance, referring to FIGS. 11A and B, the keel 28 is illustrated in accordance with an alternative embodiment, it being appreciated that the keel 30 can be similarly constructed. The keel 28 is constructed substantially as described above, however one of the wings (wing 54 as illustrated) extends longitudinally out from the keel body 42, and thus defines a laterally outer surface 55 that is coplanar with the outer surface 43 of the keel body 42 along its entire longitudinal length. Thus, the distal region 58 is not outwardly flared in the lateral direction, and in fact does not extend in a direction having a lateral component, but rather extends longitudinally rearward toward the distal end 13. The opposing wing 56 can include the flared region 60 in the manner described above.

Figure 12A:
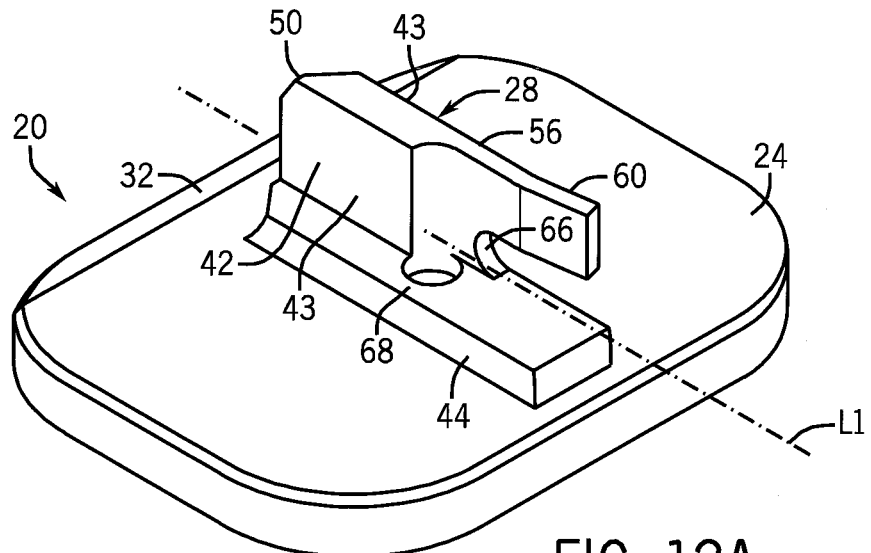
FIG. 12A is a perspective view of an intervertebral implant constructed in accordance with yet another alternative embodiment.
Figure 12B:
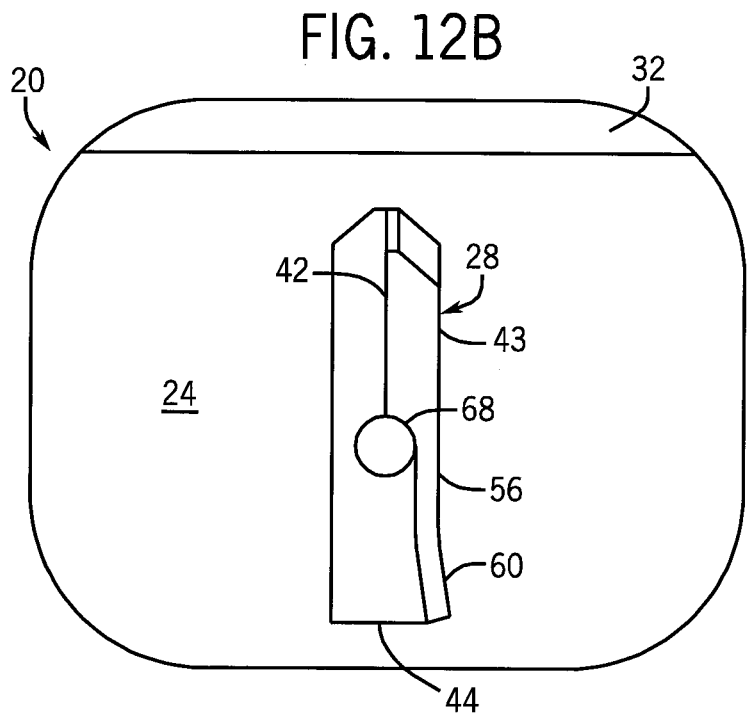
FIG. 12B is a top plan view the intervertebral implant illustrated in FIG. 12A.

Referring now to FIGS. 12A-B, in accordance with another alternative embodiment, at least one or both of the keels 28 and 30 is devoid of one of the distal regions of the wings, and is further devoid of an entire one of the wings. For instance, as illustrated, the keel 28 is constructed substantially as described above, however the keel 28 is devoid of one of the wings (wing 54 as illustrated). The keel body 42 can further be devoid of the entire lateral portion of the keel body 42 that would extend transversely out from the base 44 at a location on the same lateral side as the missing wing 54 with respect to a longitudinal axis L1 that extends centrally through the endplate 20. The opposing wing 56 can include the flared region 60 in the manner described above.

It should be appreciated that the keels 28 and 30 constructed in accordance with any of the embodiments described herein defines a maximum lateral width defines as the lateral distance between opposing laterally outermost surfaces. For instance, as illustrated in FIG. 2, the maximum lateral width of the keel 28 extends laterally between the laterally outer surfaces of the flared regions 58 and 60 at the distal edges of the flared regions 58 and 60. As illustrated in FIGS. 11A-B, the maximum width is illustrated as extending between the laterally outer surface of the flared region 60 at the distal edge of the flared region 60 and the laterally outer surface 55 of the wing 54. As illustrated in FIGS. 12A-B, the maximum width is illustrated as extending between the laterally outer surface of the flared region 60 at the distal end of the flared region 60 and the laterally outer surface 43 of the keel body 42. The maximum width of the keels 28 and 30 in each of the above-described embodiments can be the same as, greater than, or less than, the maximum widths in any of the other embodiments. Accordingly, the keels 28 and 30 can fit into the same sized slot 28, or differently sized slots as desired.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

What is claimed is:

1. An orthopedic implant configured to be anchored into boney tissue, the implant including:
    an endplate configured to be inserted into the boney tissue along a longitudinal forward direction, the endplate presenting a bone contacting surface, and a keel extending out from the bone contacting surface and configured to be disposed in a slot formed into the boney tissue, the keel including a base that extends out from the bone contacting surface, a keel body supported by the base, and a wing extending in a longitudinal rearward direction from the keel body, the wing spaced from the base in a transverse direction that is substantially perpendicular to the longitudinal forward direction by a void, the keel body having a side wall that faces the boney tissue that defines the slot, the wing including a flared portion with an outer surface that is configured to contact the boney tissue that defines the slot, the outer surface extending outward in a lateral direction that is angularly offset to both the longitudinal forward direction and the transverse direction relative to the side wall.

2. The orthopedic implant as recited in claim 1, wherein the flared portion is spaced from the bone contacting surface by a void.

3. The orthopedic implant as recited in claim 2, wherein the flared portion is flexible and configured to move with respect to the bone contacting surface.

4. The orthopedic implant as recited in claim 2, wherein keel body extends outward from the base.

5. The orthopedic implant as recited in claim 4, wherein the flared portion is flexible so as to move with respect to the base.

6. The orthopedic implant as recited in claim 5, wherein the base comprises an engagement surface configured to abut an insertion tool so as to receive a longitudinally forward biasing force.

7. The orthopedic implant as recited in claim 1, wherein the wing is a first wing, the implant further comprising a second wing laterally spaced from the first wing.

8. The orthopedic implant as recited in claim 7, wherein the flared portion is a first flared portion, and the second wing comprises a second flared portion that projects laterally outward in a direction opposite the first flared portion.

9. The orthopedic implant as recited in claim 8, wherein the first and second flared portions are configured to flex toward each other.

10. The orthopedic implant as recited in claim 9, wherein the first and second wings further comprise respective engagement surfaces configured to receive a force from an instrument that biases the first and second flared portions and toward each other.

11. The orthopedic implant as recited in claim 10, wherein the engagement surfaces extend from the wings at a location disposed between the flared portions 12. The orthopedic implant as recite in claim 1, wherein the implant is an intervertebral implant.

13. The orthopedic implant as recited in claim 1, wherein the lateral direction is substantially perpendicular to the longitudinal forward direction.

14. An orthopedic implant configured to be anchored into boney tissue, the implant including:
an endplate configured to be inserted into the boney tissue along a longitudinal forward direction, the endplate presenting a bone contacting surface, and a keel extending out from the bone contacting surface in a transverse direction and configured to be disposed in a slot formed into the boney tissue, the keel including a keel body and a wing extending rearward from the keel body, and a base extending out from the bone contacting surface in the transverse direction such that the wing is spaced from the base in the transverse direction, the wing including an outer surface that is configured to contact the bone tissue that defines the slot, wherein the wing is flexible such that when the keel is inserted in the slot the outer surface contacts the boney tissue causing the wing to move relative to the keel body.

15. The orthopedic implant as recited in claim 14, wherein the wing is spaced from the base by a void.

16. The orthopedic implant as recited in claim 15, wherein the wing is a first wing, the implant further comprising a second wing spaced laterally from the first wing.

17. The orthopedic implant as recited in claim 16, wherein each wing further comprises a flared portion that projects laterally outward in a direction away from each other.

18. The orthopedic implant as recited in claim 17, wherein the first and second wings further comprise respective engagement surfaces configured to receive a force from an instrument that biases the flared portions toward each other.

19. The orthopedic implant as recited in claim 14, wherein the implant is an intervertebral implant.

20. The orthopedic implant as recited in claim 14, wherein the transverse direction is substantially perpendicular to the longitudinal forward direction.

21. An endplate of a vertebral implant, the endplate configured to be inserted into an intervertebral space along a longitudinal forward direction, the endplate presenting a bone contacting surface and a keel extending out from the bone contacting surface and configured to be disposed in a slot formed in a vertebra, the keel including a base, a keel body extending up from the base such that the base extends in a rearward direction from the keel body, and a wing extending in the rearward direction from the keel body, the wing spaced from the base in a transverse direction that is angularly offset from the longitudinal forward direction by a void, the keel body having a side wall that faces the boney tissue, the wing including a flexible flared portion with an outer surface that is configured to contact the boney tissue, the outer surface projecting laterally outward relative to the side wall in a direction offset from each of the longitudinal forward direction, the rearward direction and the transverse direction.

22. An orthopedic implant configured to be anchored into boney tissue, the implant including:
an endplate configured to be inserted into the boney tissue along a longitudinal forward direction, the endplate presenting a bone contacting surface, and a keel extending out from the bone contacting surface and configured to be disposed into a slot formed into the boney tissue, the keel including a keel body and first and second wings, each of the first and second wings being laterally spaced from one another, configured to flex toward one another, and extending rearward from the keel body, the first and second wings including a first flared portion and a second flared portion, respectively, that each project laterally outward in opposite directions with respect to a longitudinally rearward direction, the first and second wings further including respective engagement surfaces configured to receive a force from an instrument that biases the first and second flared portions toward each other, the engagement surfaces each extending from the first and second wings at a location disposed between the first and second flared portions, and the first and second flared portions being spaced from the bone contacting surface by a void.

* * * * *